US012778547B2

(12) United States Patent
Govari et al.

(10) Patent No.: US 12,778,547 B2
(45) Date of Patent: Nov. 3, 2026

(54) RECONSTRUCTING A 4D SHELL OF A VOLUME OF AN ORGAN USING A 4D ULTRASOUND CATHETER

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 525 days.

(21) Appl. No.: 17/357,231

(22) Filed: Jun. 24, 2021

(65) Prior Publication Data

US 2022/0409172 A1 Dec. 29, 2022

(51) Int. Cl.

*A61B 8/00* (2006.01)
*A61B 8/02* (2006.01)
*A61B 8/12* (2006.01)

(52) U.S. Cl.

CPC .............. *A61B 8/4254* (2013.01); *A61B 8/02* (2013.01); *A61B 8/12* (2013.01); *A61B 8/4494* (2013.01);

(Continued)

(58) Field of Classification Search

CPC ......... A61B 8/463; A61B 8/4494; A61B 8/12; A61B 8/02; A61B 8/4254; A61B 8/465; A61B 8/5207; A61B 8/5238; A61B 8/0841; A61B 8/523; A61B 8/5261; A61B 8/5269; A61B 8/543; A61B 8/0883;

(Continued)

(56) References Cited

U.S. PATENT DOCUMENTS 6,059,731 A 5/2000 Seward et al.
6,216,027 B1 * 4/2001 Willis ................. A61B 5/6855 600/462

(Continued)

FOREIGN PATENT DOCUMENTS

JP 2006-255083 A 9/2006
JP 2006-521146 A 9/2006

(Continued)

OTHER PUBLICATIONS

Vitulano, et al., "Technology Update: Intracardiac Echocardiography—A Review of the Literature," Medical Devices (Auckland, NZ) vol. 8 (2015), pp. 231-239.

(Continued)

*Primary Examiner* — Peter Luong

(74) *Attorney, Agent, or Firm* — Smith, Gambrell & Russell LLP

(57) ABSTRACT

A medical system includes an ultrasound probe and a processor. The ultrasound probe is configured for insertion into an organ of a body and includes (i) a two-dimensional (2D) ultrasound transducer array, and (ii) a sensor configured to output signals indicative of a position and orientation of the 2D ultrasound transducer array inside the organ. The processor is configured to (a) using the signals output by the sensor, register multiple ultrasound image sections, acquired by the 2D ultrasound transducer array, with one another, (b) produce a union of the multiple registered ultrasound image sections, to form a rendering of at least a portion of the organ, and (c) present the rendering to a user.

16 Claims, 4 Drawing Sheets

(52) U.S. Cl.
CPC .............. *A61B 8/463* (2013.01); *A61B 8/465* (2013.01); *A61B 8/5207* (2013.01); *A61B 8/5238* (2013.01)

(58) Field of Classification Search
CPC ..... A61B 8/4488; A61B 8/483; A61B 8/5246; G01S 7/52065; G01S 7/52046; G01S 15/8993; G01S 15/8925
See application file for complete search history.

(56) References Cited

U.S. PATENT DOCUMENTS

| | | | | |
|---|---|---|---|---|
| 6,332,089 | B1 | 12/2001 | Acker et al. | |
| 6,618,612 | B1 | 9/2003 | Acker et al. | |
| 6,896,657 | B2 | 5/2005 | Willis | |
| 7,878,977 | B2 | 2/2011 | Mo et al. | |
| 8,057,394 | B2 | 11/2011 | Dala-Krishna | |
| 8,285,364 | B2 | 10/2012 | Barbagli | |
| 9,179,890 | B2 | 11/2015 | Ionasec et al. | |
| 9,980,786 | B2 | 5/2018 | Saul et al. | |
| 10,537,306 | B2 | 1/2020 | Schaer et al. | |
| 11,039,883 | B1 | 6/2021 | Boveja et al. | |
| 2002/0065455 | A1 | 5/2002 | Ben-Haim et al. | |
| 2003/0120150 | A1 | 6/2003 | Govari | |
| 2004/0068178 | A1 | 4/2004 | Govari et al. | |
| 2005/0033173 | A1* | 2/2005 | Von Behren | A61B 8/00 600/443 |
| 2006/0182320 | A1 | 8/2006 | Peszynski et al. | |
| 2006/0239540 | A1 | 10/2006 | Serra | |
| 2006/0241434 | A1 | 10/2006 | Shimazaki | |
| 2006/0241445 | A1* | 10/2006 | Altmann | G06T 7/12 600/443 |
| 2007/0167821 | A1 | 7/2007 | Lee et al. | |
| 2008/0125658 | A1 | 5/2008 | Lee et al. | |
| 2008/0146941 | A1* | 6/2008 | Dala-Krishna | A61B 8/4254 600/466 |
| 2008/0287778 | A1 | 11/2008 | Li et al. | |
| 2008/0300487 | A1* | 12/2008 | Govari | A61B 8/483 600/443 |
| 2009/0076386 | A1 | 3/2009 | Sirivolu et al. | |
| 2009/0304250 | A1* | 12/2009 | McDermott | A61B 8/463 382/131 |
| 2010/0179428 | A1* | 7/2010 | Pedersen | G09B 23/286 600/443 |
| 2012/0183188 | A1* | 7/2012 | Moriya | G16H 30/20 382/128 |
| 2019/0223958 | A1 | 7/2019 | Kohli et al. | |
| 2019/0336110 | A1 | 11/2019 | Kustra et al. | |
| 2020/0061340 | A1 | 2/2020 | Mixter et al. | |

FOREIGN PATENT DOCUMENTS

| | | |
|---|---|---|
| JP | 6312938 B | 4/2018 |
| WO | WO9605768 | 2/1996 |
| WO | WO2020/055506 | 3/2020 |

OTHER PUBLICATIONS

Dausch et al., "Real-Time 3D Intracardiac Echo of the Mitral Value Using a Novel Live Volumetric Imaging Catheter," Journal of the American College of Cardiology, Mar. 2013, vol. 61, No. 10.

Wildes, D. et al., "4D ice: a 2D Array Transducer With Integrated ASIC in a 10-Fr Catheter for Real-Time 3D Intracardiac Echocardiography," in IEEE Transactions on Ultrasonics, Ferroelectrics, and Frequency Control, vol. 63, No. 12, pp. 2159-2173, Dec. 2016, doi: 0.1109/TUFFC.2016.2615602.

Extended European Search Report from corresponding EP application 22180637.5-1126 dated Nov. 17, 2022.

Packer, D. L. et al. "New generation of electro-anatomic mapping: full intracardiac ultrasound image integration", Europace, vol. 10, No. Supplement 3, Nov. 1, 2008; pp. iii35-iii41.

Gao, Gang; "Real-time compounding of three-dimensional transesophageal echocardiographic voulumes: The phantom study"; Sep. 6, 2009.

European Office Action dated Nov. 28, 2024 for Application No. 22180637.5; 6 pages.

* cited by examiner

RECONSTRUCTING A 4D SHELL OF A VOLUME OF AN ORGAN USING A 4D ULTRASOUND CATHETER

FIELD OF THE INVENTION

The present invention relates generally to invasive medical instruments, and particularly to intra-body medical probes and methods employing ultrasound.

BACKGROUND OF THE INVENTION

Invasive ultrasound techniques have been previously proposed to serve as a tool to assess an anatomy within the body. For example, Nicola, et al., describe in a paper titled "Technology Update: Intracardiac Echocardiography—A Review of the Literature," Medical Devices (Auckland, NZ) volume 8 (2015), pages 231-239, a volumetric 3D intracardiac ultrasound system for improving the visualization of valvular, perivalvular, and aortic structures. The paper discusses how intra cardiac echocardiography could give additional information compared to traditional electroanatomic mapping system, defining, for example, not only the relevant arrhythmogenic myocardial areas but also the wall thickness before ablation.

As another example, Dausch et al., describe in a paper titled "Real-Time 3D Intracardiac Echo of the Mitral Value Using a Novel Live Volumetric Imaging Catheter," Journal of the American College of Cardiology, March, 2013, volume 61, number 10, a 14F catheter containing an ultrasound transducer matrix phased array with 256 elements. The catheter is shown to acquire in vivo intra cardiac echocardiography images of the left ventricle and mitral valve. The catheter provided real-time 3D intracardiac ultrasound imaging with the combined desired features of full volume views (up to 80×80 degrees), deep scan depth (8-10 cm), high frame rate (20-30 volumes per second) and good resolution.

U.S. Pat. No. 7,878,977 describes a transducer array that includes two or more sub-arrays that move relative to each other. Position sensors on each of the sub-arrays provide spatial coordination for beamforming and/or image forming to yield extended field of view and high image resolution. The adaptable transducer array, such as mounted on a flexible transducer housing, allows the array to better conform to the patient during internal or external use. In an embodiment, a transducer array is rotated to scan a volume for 3D imaging. The array scans a plane at each rotational position or as the array rotates. The data for the scan planes is assembled based on the position of the sub-arrays during acquisition. A 3D representation is assembled from the data.

U.S. Pat. No. 6,896,657 describes systems, methods and devices for imaging an internal anatomical structure. Ultrasound image data of the anatomical structure is acquired within a first coordinate system, and graphical data (e.g., sites of interest) is acquired in a second coordinate system. The location of an ultrasound transducer within the first coordinate system and a second coordinate system is determined, and a transformation between the first and second coordinate systems is then performed based on the location of the ultrasound transducer within the first and second coordinate systems. Using this transformation, the ultrasound image data, which has previously been acquired in the first coordinate system, can be registered and displayed within the second coordinate system, along with graphical data. Or the graphical data, which has previously been acquired in the second coordinate system, can be registered and displayed within the first coordinate system, along with the image data. In this manner, the image and graphical data can be easily displayed together independent of any movement by the imaging device that acquires the image data.

U.S. Pat. No. 8,285,364 describes an automated medical system comprising a first instrument assembly including a first ultrasound transducer having a first transducer field of view that transmits and receives ultrasound signals in imaging planes disposed circumferentially about a guide instrument, and a second instrument assembly including a second ultrasound transducer having a second transducer field of view coupled to one of a second flexible guide instrument and a working instrument. A computing system is operatively coupled to the respective first and second transducers and configured to determine a relative spatial orientation of the respective first and second transducers based at least in part on detecting a signal transmitted by one of the first and second transducers and received by the other of the first and second transducers, the received signal having an amplitude indicating the receiving one of the transducers is in the field of view of the transmitting one of the transducers.

SUMMARY OF THE INVENTION

An embodiment of the present invention that is described hereinafter provides a medical system including an ultrasound probe configured for insertion into an organ of a body, and a processor. The ultrasound probe includes (i) a two-dimensional (2D) ultrasound transducer array, and (ii) a sensor configured to output signals indicative of a position and orientation of the 2D ultrasound transducer array inside the organ. The processor is configured to (a) using the signals output by the sensor, register multiple ultrasound image sections, acquired by the 2D ultrasound transducer array, with one another, (b) produce a union of the multiple registered ultrasound image sections, to form a rendering of at least a portion of the organ, and (c) present the rendering to a user.

In some embodiments, the rendering includes a four-dimensional (4D) rendering of at least the portion of the organ, and the processor is configured to produce the 4D rendering by forming multiple instances of the union for different phases of a given heartbeat.

In some embodiments, the processor is configured to produce the union from multiple registered ultrasound image sections acquired in a given cardiac-cycle phase over multiple heartbeats.

In an embodiment, the processor is further configured to incorporate into the rendering a newly acquired image section from a known location, using the signals output by the sensor.

In another embodiment, the processor is further configured to incorporate into the rendering a graphical indication at a known location, using the signals output by the sensor.

In some embodiments, the graphical indication is an icon. In other embodiments, the graphical indication is of an artificial element.

In an embodiment, the processor is further configured to provide multi-planar reformation (MPR) views of the portion of the organ, using the signals output by the sensor.

There is additionally provided, in accordance with another embodiment of the present invention, a medical imaging method including inserting an ultrasound probe into an organ of a body, the ultrasound probe including (i) a two-dimensional (2D) ultrasound transducer array, and (ii) a sensor configured to output signals indicative of a position and orientation of the 2D ultrasound transducer array inside the organ. Using the signals output by the sensor, multiple ultrasound image sections are registered with one another, the sections acquired by the 2D ultrasound transducer array. A union of the multiple registered ultrasound image sections is produced, to form a rendering of at least a portion of the organ. The rendering is presented to a user.

The present invention will be more fully understood from the following detailed description of the embodiments thereof, taken together with the drawings in which:

DETAILED DESCRIPTION OF EMBODIMENTS

Overview

Figure 1:
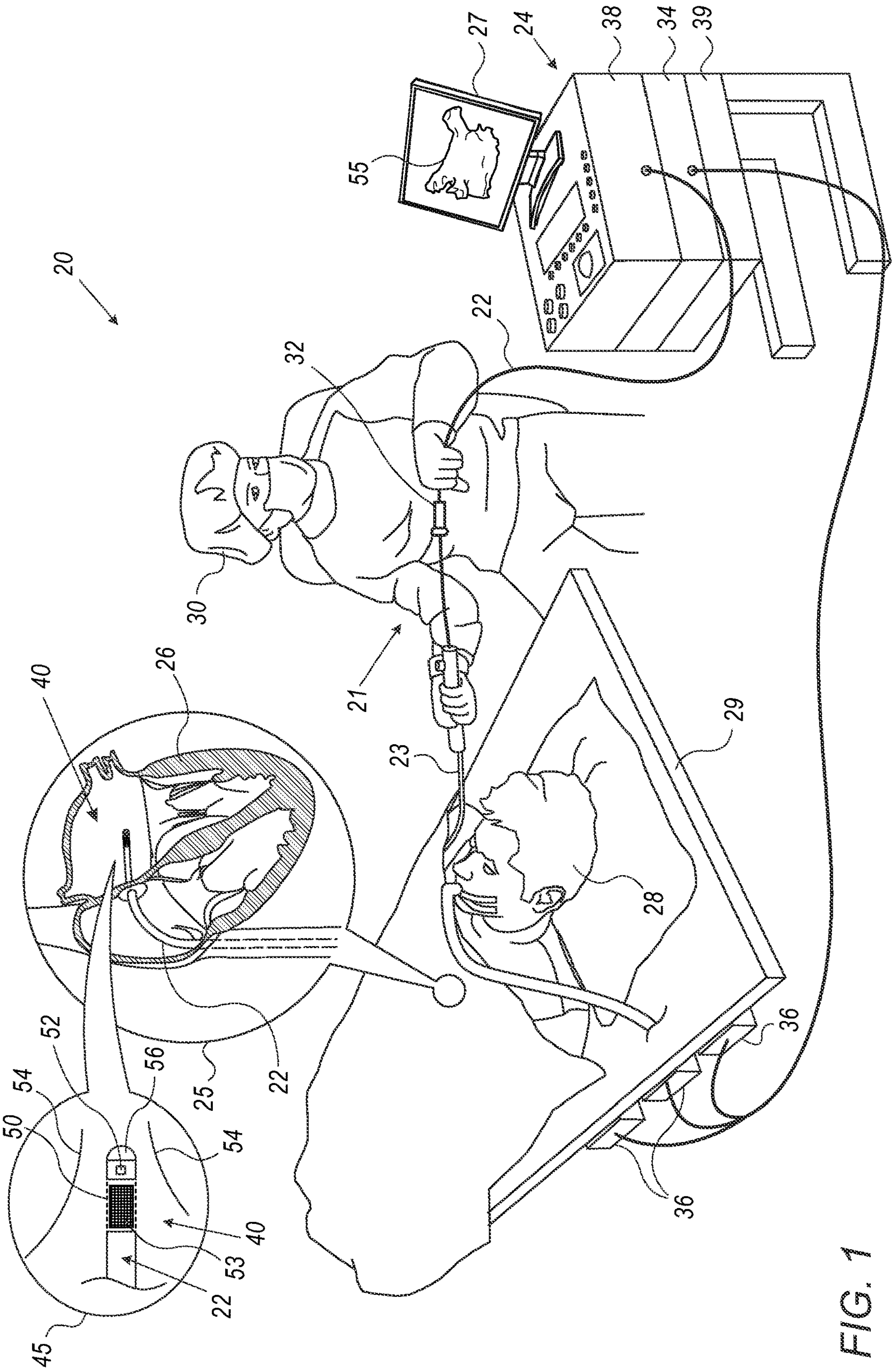
FIG. 1 is a schematic, pictorial illustration of a catheter-based ultrasound imaging system using a catheter with a distal end assembly comprising a 2D ultrasound-array and a location sensor, in accordance with an embodiment of the present invention.

Embodiments of the present invention that are described herein provide methods and systems that use a probe, such as a catheter, having a two-dimensional (2D) array of ultrasound transducers for producing three-dimensional (3D) or four-dimensional (4D) ultrasound images. In the present context, the term "3D ultrasound image" refers to an ultrasound image that represents a certain volume in three dimensions. The term "4D ultrasound catheter" refers to a catheter incorporating a 2D array of ultrasound transducers. The term "4D ultrasound image" refers to a time-series of 3D ultrasound images of a certain volume acquired by the 2D array. A 4D image can be regarded as a 3D movie, the fourth dimension being time. Another way of describing 4D image (or rendering) is as a time-dependent 3D image (or rendering). Where used in the heart, a 4D ultrasound catheter may be referred to as "4D Intracardiac Echocardiography (ICE)" catheter.

In the embodiments disclosed herein, the catheter also comprises an integral location sensor, such as a magnetic position sensor, that is pre-registered with the 2D array based on the known relative position and orientation on the catheter shaft between the location sensor and the 2D array. The 2D array produces a 3D sector-shaped ultrasound beam occupying a defined solid angle; (such a beam is referred to herein as a "wedge," as opposed to a 1D array "fan"). The 2D array is thus able to image a three-dimensional 3D section of an inner wall of an organ, such as of a cardiac chamber. Because of the integral location sensor, and its pre-registration with the 2D array, the spatial coordinates of every voxel in the imaged section are known.

In one embodiment, the phases of the transducers of the 2D array are adjusted to provide beam steering. In this way, different sections of the inner wall can be imaged by sweeping the ultrasound wedge. The wedge can be swept in two dimensions, so that an entire sub-shell of the chamber inner surface (formed from multiple sections) can be imaged.

To image a large portion of the chamber, or even the entire chamber, the catheter is moved to other locations to image other sub-shells in order to produce a plurality of sub-shells. These sub-shells may be formed into a "union." Since the spatial coordinates of each voxel in a sub-shell are known from the location sensor, computationally intensive algorithms that would otherwise be required, such as stitching, are not required. Nor is "intersection" of the sub-shells necessary. The union of the sub-shells thus forms a 3D rendering of the chamber.

The plurality of sub-shells may be produced in a gated manner, over several heartbeats, during a cardiac phase when the heart is quiescent (e.g., such as during peak diastoles). Additionally or alternatively, a plurality of sub-shells may be produced at different phases of a given heartbeat to provide a 4D image (e.g., a moving 3D rendering) of the chamber.

In addition to imaging the inner surface of the chamber wall, the 2D catheter can also image the outer surface. Thus, detail and structure of the wall itself can be imaged.

In an embodiment, a processor selects a specific imaged structure from a 3D or 4D ultrasound image and incorporates it into an existing surface rendering. The operator of the catheter may select a specific structure. Because the 3D or 4D image is automatically registered in position and orientation by the location sensor in the catheter, the processor of the system is able to correctly incorporate the selected structure into an existing surface rendering. In this way, for example, the operator may more easily identify specific anatomic structures (e.g., within cardiac chamber images) in an ultrasound overlayed with color values of another parameter, such as the electrophysiological parameter of local activation time (LAT).

Anatomic structures that may be incorporated into the heart chamber surface image comprise, for example, the mitral valve, a pulmonary vein, and/or the left atrial appendage.

Additionally or alternatively, after selection of the 3D or 4D image, the operator may choose an icon to be incorporated rather than the 4D image itself. The incorporation simplifies the interpretation of the surface rendering. For example, given a detailed ultrasound rendering of a wall of a heart chamber, either automatically, or using guidance from an operator of the catheter, a specific element (e.g., artificial elements such as a catheter, a surgical staple, or a planned path of interest for ablation) is identified in the image. Once identified, a graphical representation (e.g., an icon) of the element is inserted into the heart chamber image.

The incorporation of anatomic structures and/or icons, either automatically or by user selection, enhances the operator's ability to interpret the surface rendering.

In other embodiments of the current invention, the processor can improve the quality of "raw" gray level images by applying transfer functions to reduce noise and provide a better rendering of the 3D volume. The transfer functions may also be adjusted, e.g., by "banding" different values of gray levels, so that the final images better distinguish between different tissue types.

Once the 3D volume has been formed, the processor may generate a planar slice of the volume, using any operator-selected plane, to provide an alternative view of the chamber. For example, the processor may provide multi-planar reformation (MPR) views.

System Description

FIG. 1 is a schematic, pictorial illustration of a catheter-based ultrasound imaging system 20 using a catheter 21 with a distal end assembly 40 comprising a 2D ultrasound-array 50 and a location sensor 52, in accordance with an embodiment of the present invention. Integral location sensor 52 is pre-registered with the 2D array 50 of catheter 21.

Specifically, sensor 52 is configured to output signals indicative of a position and orientation of the 2D ultrasound transducer array 52 inside the organ. A processor of the system is configured to, using the signals output by the sensor, register multiple ultrasound image sections, acquired by the 2D ultrasound transducer array 50, with one another.

As seen, distal end assembly 40 is fitted at the distal end of a shaft 22 of the catheter. Catheter 21 is inserted through a sheath 23 into a heart 26 of a patient 28 lying on a surgical table 29. The proximal end of catheter 21 is connected to a control console 24. In the embodiment described herein, catheter 21 may is used for ultrasound-based diagnostic purposes, although the catheter may be further used to perform a therapy such as electrical sensing and/or ablation of tissue in heart 26, using, for example, a tip electrode 56.

A physician 30 navigates distal end assembly 40 of catheter 21 to a target location in heart 26 by manipulating shaft 22 using a manipulator 32 near the proximal end of the catheter.

In an embodiment, 2D ultrasound-array 50, shown in detail in an inset 25, is configured to image a left atrium of heart 26. As seen in an inset 45, ultrasound-array 50 comprises a 2D array 50 of multiple ultrasound transducers 53. Inset 45 shows ultrasound-array 50 navigated to an inner wall 54 of a pulmonary vein of the left atrium. In this embodiment, 2D array 50 is an array of 32×64 ultrasound transducers. The 2D array is able to image a section of the inner wall of the ostium. Because of the integral location sensor, and its pre-registration with the 2D array, the spatial coordinates of every pixel in the imaged section are known by the system. An example of a suitable 2D array is described in D. Wildes et al., "4-D ICE: A 2-D Array Transducer With Integrated ASIC in a 10-Fr Catheter for Real-Time 3-D Intracardiac Echocardiography," in IEEE Transactions on Ultrasonics, Ferroelectrics, and Frequency Control, vol. 63, no. 12, pp. 2159-2173, December 2016, doi: 10.1109/TUFFC.2016.2615602, which is incorporated herein by reference in its entirety.

Control console 24 comprises a processor 39, typically a general-purpose computer, with suitable front end and interface circuits 38 for receiving signals from catheter 21, as well as for, optionally, applying treatment via catheter 21 in heart 26 and for controlling the other components of system 20. Console 24 also comprises a driver circuit 34, configured to drive magnetic field generators 36.

During the navigation of distal end 22 in heart 26, console 24 receives position and direction signals from location sensor 52 in response to magnetic fields from external field generators 36. Magnetic field generators 36 are placed at known positions external to patient 28, e.g., below table 29 upon which the patient is lying. These position and direction signals are indicative of the position and direction of 2D ultrasound-array 50 in a coordinate system of the position tracking system.

The method of position and direction sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

In some embodiments, processor 39 may be configured to operate array 50 in a "sweeping mode" to image an entire cardiac camber or a portion thereof, as described below. In an embodiment, the imaged cardiac chamber (e.g., a left atrium) is presented to physician 30 by processor 39 on a monitor 27, e.g., in as a volume rendering 55.

Processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise additional components and perform non-cardiac catheterizations.

Using a 2D Ultrasound Catheter to Build a 4D Shell of a Volume of an Anatomy

Figure 2:
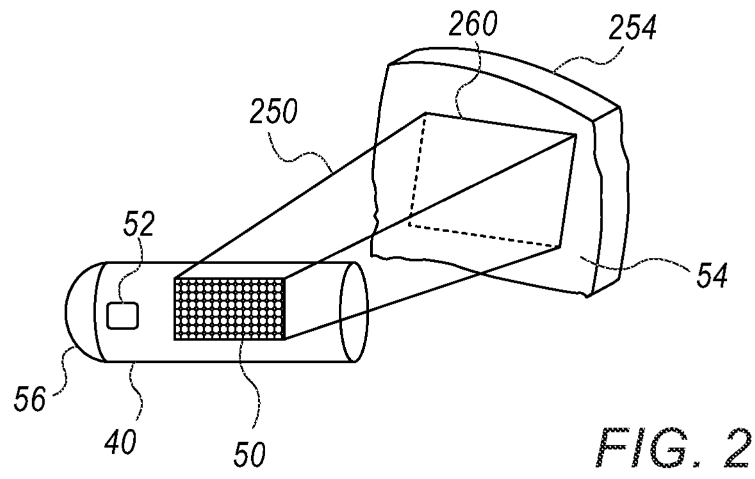
FIG. 2 is a schematic, pictorial illustration of acquisition of an imaged section of an inner wall of an organ using an ultrasound beam emitted by the catheter of the system of FIG. 1, in accordance with an embodiment of the present invention.

FIG. 2 is a schematic, pictorial illustration of acquisition of an imaged section 260 of inner wall 54 of an organ 254 using an ultrasound beam 250 emitted by catheter 21 of system 20 of FIG. 1, in accordance with an embodiment of the present invention. As seen, the use of 3D wedge 250 enables simultaneous acquisition of the section 260. Using location sensor 52, the geometry of ultrasound wedge 250 can be registered with a coordinate system of the location tracking system of system 20.

Figure 3:
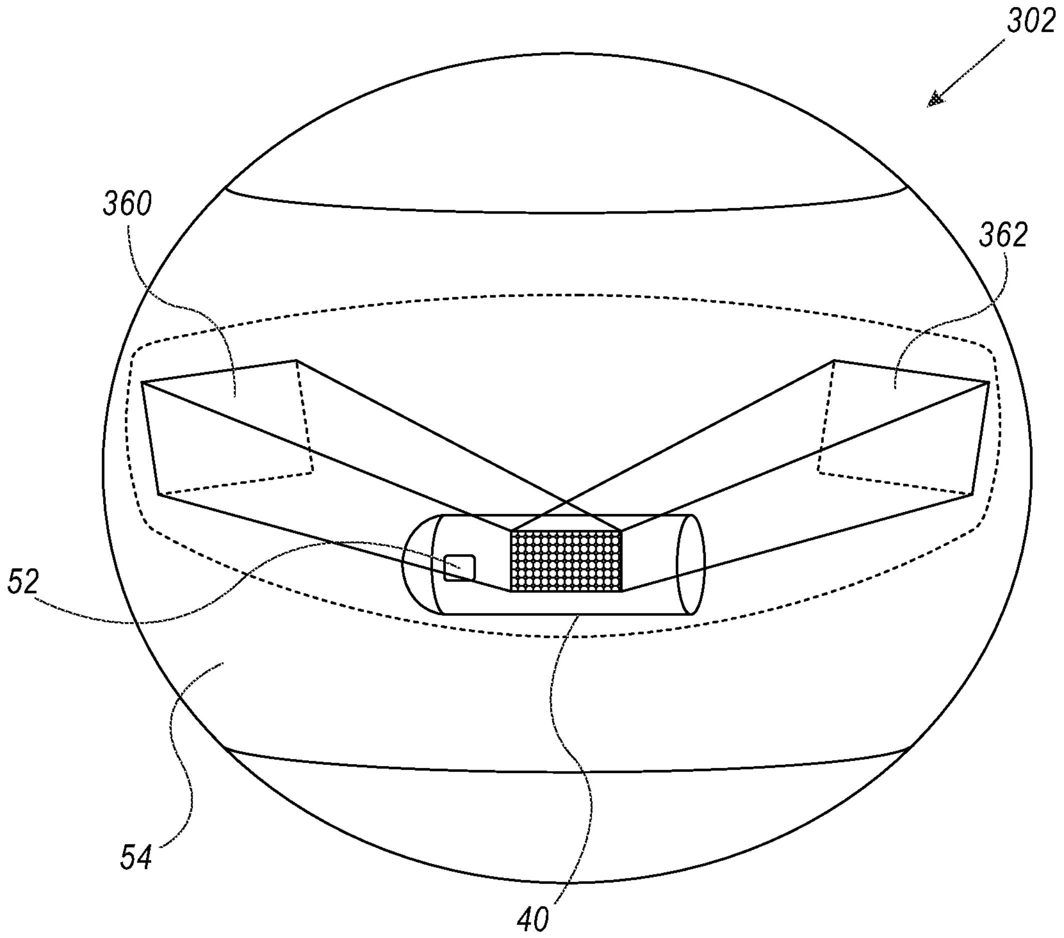
FIG. 3 is a schematic, pictorial illustration of an ultrasound acquisition mode comprising spatially sweeping the ultrasound beam of FIG. 2 over an inner wall of an organ, in accordance with an embodiment of the present invention.

FIG. 3 is a schematic, pictorial illustration of an ultrasound acquisition mode comprising spatially sweeping ultrasound beam 250 of FIG. 2 over inner wall 54 of an organ, in accordance with an embodiment of the present invention. In the shown embodiment, an entire sub-shell 302 of inner wall 54 of the organ is imaged by placing catheter 21 of system 20 of FIG. 1 at a given location and steering the ultrasound wedge electronically.

To this end, processor 39 adjusts the phases of the 2D transducers so that ultrasound wedge 250 is swept to image different sections (e.g., sections 360, 362) of the inner wall can be imaged. Wedge 250 can be swept in two dimensions, so that an entire sub-shell 302 of the inner surface (formed from multiple sections) of the organ can be imaged. In this manner, the entire sub-shell 302 is imaged while distal end assembly 40 is stationary at the same position and orientation. Additional sub-shells or the entire cardiac chamber may be imaged when the physician causes the catheter shaft, onto which the 2D array is mounted, to translate, deflect, and/or rotate such that additional portions of the cardiac chamber come within the field of view of ultrasound wedge 250. Exemplary intravascular catheters and imaging assemblies that enable such deflection and rotation are described in detail in U.S. Pat. Nos. 9,980,786; 10,537,306; and U.S. Patent Publication No. 2020-0061340 A1, whose disclosures are all incorporated herein by reference.

The pictorial illustration shown in FIG. 3 is chosen purely for the sake of conceptual clarity. The disclosed catheter with its ultrasound array may be applied using other scanning modes.

Figure 4:
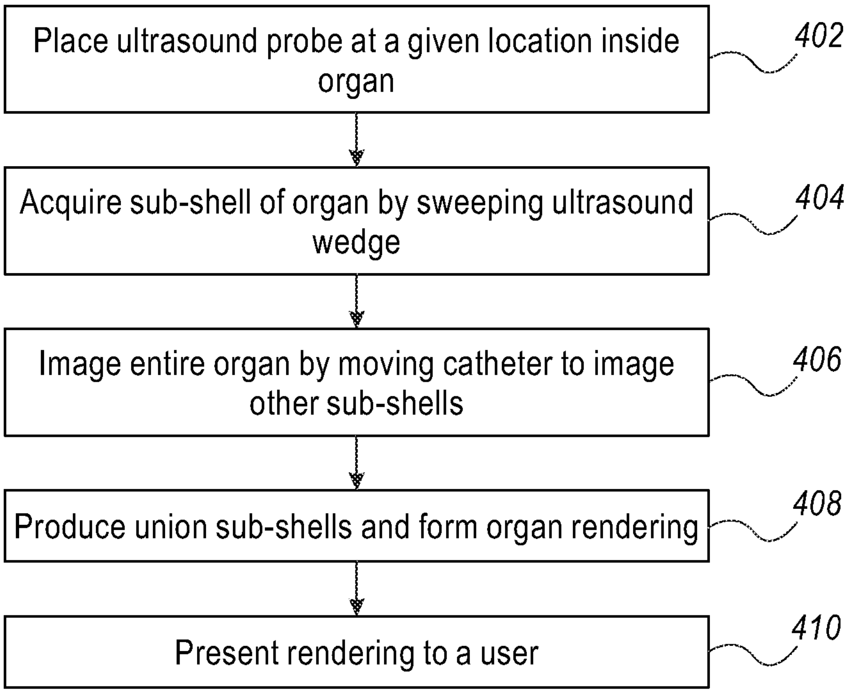
FIG. 4 is a flow chart that schematically illustrates a method for imaging an inner wall of an organ using the catheter-based ultrasound imaging system of FIG. 1, in accordance with an embodiment of the present invention.

FIG. 4 is a flow chart that schematically illustrates a method for imaging an inner wall of an organ using catheter-based ultrasound imaging system 20 of FIG. 1, in accordance with an embodiment of the present invention. The procedure begins by placing ultrasound array 50 at a given location inside the organ, at an ultrasound probe placement step 402.

Next, processor 39 acquires ultrasound sections (such as sections 360, 362) by sweeping ultrasound wedge 250 as described above, at a beam steering and acquisition step 404. The wedge can be swept in two dimensions, so that a whole sub-shell of the chamber's inner surface (formed from multiple sections) can be imaged. Alternatively, sweeping can be limited to a single dimension if desired.

Next, in order to image the entire chamber (or any suitable portion of the chamber that is larger than a single sub-shell), physician 30 moves (and/or rotates) the catheter to one or more other locations to image other sub-shells, thus producing a plurality of sub-shells, at a multi-sub-shell acquisition step 406.

At an organ imaging step 408, the processor produces a union of the multiple acquired sub-shells, relying on the spatial coordinates of each pixel in a sub-shell being known from location sensor 52. The union of the sub-shells thus forms the 3D image of the chamber.

Finally, processor 39 displays the resulting surface rendering, such as rendering 425, to physician 30, at a displaying step 410.

The description above refers to the generation of a 3D image of an organ. In some embodiments, the process may be repeated at different times (e.g., at multiple different phases of the cardiac cycle) to produce a 4D image (a time series of 3D images) of the organ.

Incorporating a Selected Segment into an Existing Surface Rendering

Figure 5:
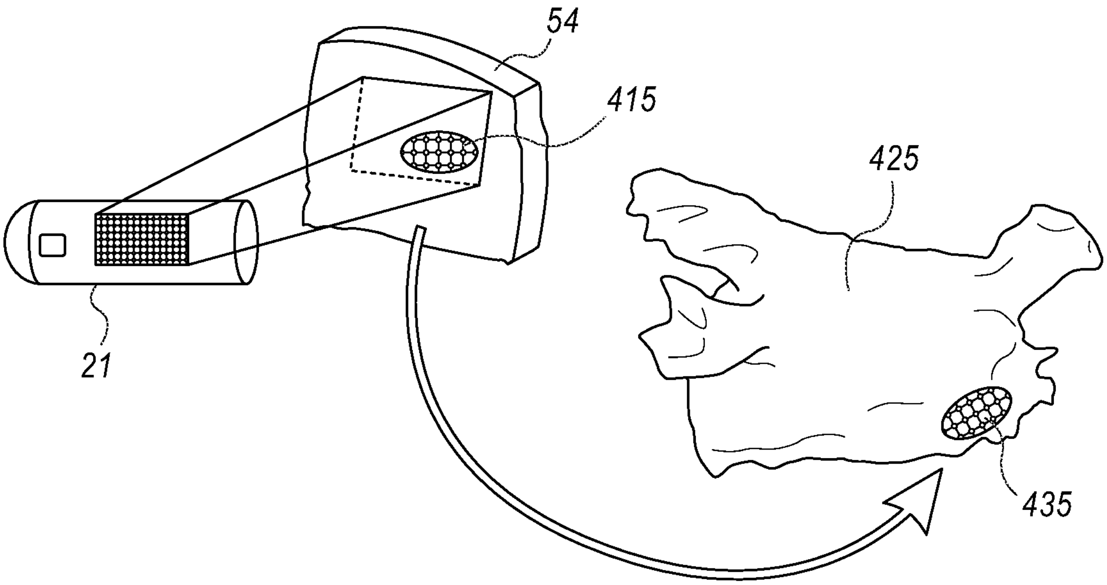
FIG. 5 is a schematic, pictorial illustration showing the incorporation of a selected ultrasound image rendering into an existing surface rendering, displayed to the physician on a monitor, in accordance with an embodiment of the present invention.

FIG. 5 is a schematic, pictorial illustration showing the incorporation of a selected ultrasound image rendering 435 into an existing surface rendering 425, displayed to the physician on a monitor, in accordance with an embodiment of the present invention.

In the shown embodiment, processor 39 selects a specific imaged structure 415 on wall 54, for example an ostium of a pulmonary vein that is imaged in high resolution during an ultrasound imaging session acquiring a 4D ultrasound image and incorporates it into an existing surface rendering 425 (e.g., into a low-resolution rendering that was taken during another 4D ultrasound imaging session). The operator of the catheter may select a specific structure 415. Because the 4D image is automatically registered in position and orientation by the location sensor in catheter 21, processor 39 of system 20 is able to correctly incorporate the selected structure into an existing surface image. In this way, for example, a user may more easily identify specific anatomic structures (e.g., left atrium rendering 425).

The example configurations shown in FIG. 5 were chosen purely for the sake of conceptual clarity. There are numerous other ways that can be used for presenting an imaged structure, such as embedding a multi-planar reformation (MPR) at the location.

Figure 6:
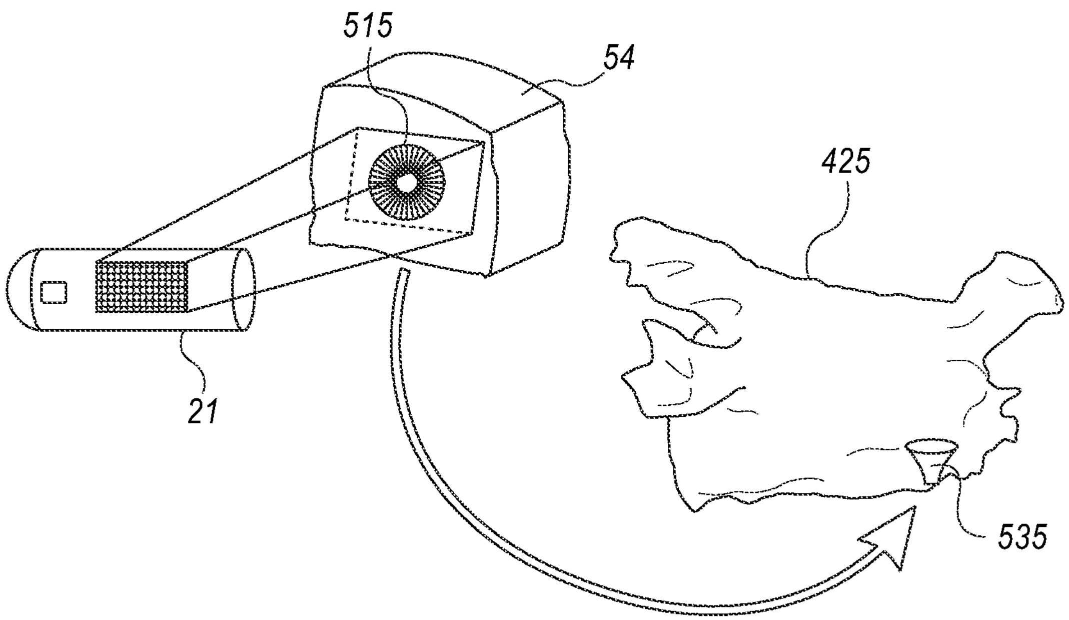
FIG. 6 is a schematic, pictorial illustration showing the incorporation of an icon into an existing surface rendering, displayed to the physician on a monitor, in accordance with an embodiment of the present invention.

FIG. 6 is a schematic, pictorial illustration showing the incorporation of an icon 535 into an existing surface rendering 425, displayed to the physician on a monitor, in accordance with an embodiment of the present invention.

In the shown embodiment, after selection of rendering 425, the operator may choose an icon to be incorporated. The incorporation enhances the interpretation of the surface images. For example, given a detailed ultrasound image of a wall 54 of a heart chamber, either automatically, or using guidance from physician 30 operating the catheter, a specific element of interest 515 (e.g., a surgical object such as a staple) is identified in the image. Once the physician identifies the element of interest, in response to physician selection, the processor inserts an icon of the element into rendering 425 of the left atrium.

Figure 7:
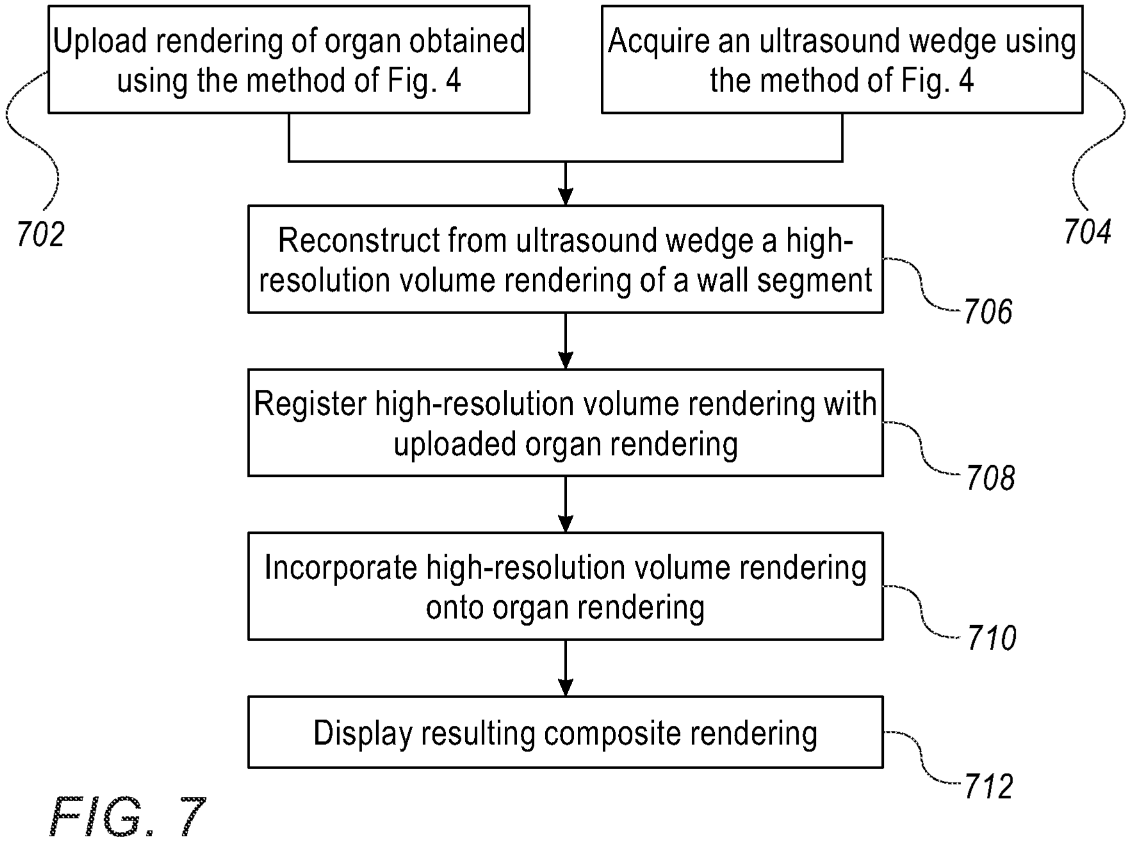
FIG. 7 is a flow chart that schematically illustrates a method for incorporating a portion of an ultrasound image and/or an icon into an existing surface rendering, displayed to the physician on a monitor, in accordance with an embodiment of the present invention.

FIG. 7 is a flow chart that schematically illustrates a method for incorporating an ultrasound rendering 435 and/or an icon 535 into an existing surface rendering 425, displayed to the physician on a monitor, in accordance with an embodiment of the present invention. The process begins by uploading rendering 425 that was generated using the method of FIG. 4, at a rendering an uploading step 702.

Next, processor 39 acquires, using catheter 21, a specific image section of a wall 54 segment 415, for example, by acquiring an ultrasound wedge 250 from a given position, direction, and orientation of array 50, as indicated by sensor 52, at a wall segment acquisition step 704.

Next the processor reconstructs from ultrasound wedge 250 ultrasound images of wall segment 415, at images segment reconstruction step 706. The reconstruction may yield, for example, a high-resolution volume rendering 435 of wall segment 415.

Next, using the indication from sensor 52, processor 39 registers high-resolution volume rendering 435 with volume rendering 425, at a registration step 708.

At an incorporation step 710, processor 39 incorporates high-resolution volume rendering 435 onto volume rendering 425, to generate a composite rendering of the organ.

Finally, processor 39 displays the resulting composite rendering, such as the one shown in FIG. 5, to physician 30, at a displaying step 712.

In another embodiment, using the registration, the processor may incorporate onto volume rendering 425 a graphical indication, such as icon 535.

In various embodiments, the processes of FIGS. 5-7 above can be applied to 3D images and/or to 4D images, as appropriate.

Although the embodiments described herein mainly address cardiac applications, the methods and systems described herein can also be used in other body organs. For example, the disclosed technique can be used with Transesophageal ultrasound device (TEE) devices visualizing the heart. As another example, the disclosed technique may be used for invasive ultrasound imaging the lung, and for visualizing liver and kidney.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:

an ultrasound probe for insertion into an organ of a body, the ultrasound probe comprising:

a two-dimensional (2D) ultrasound transducer array; and a sensor configured to output signals indicative of a position and orientation of the 2D ultrasound transducer array inside the organ; and a processor, which is configured to:

using the signals output by the sensor, register multiple three-dimensional (3D) ultrasound volumes, acquired by the 2D ultrasound transducer array, with one another;

produce a union of the multiple registered 3D ultrasound volumes, to form a rendering of at least a portion of the organ; and present the rendering to a user.

2. The medical system according to claim 1, wherein the rendering comprises a four-dimensional (4D) rendering of at least the portion of the organ, and wherein the processor is configured to produce the 4D rendering by forming multiple instances of the union for different phases of a given heartbeat.

3. The medical system according to claim 1, wherein the processor is configured to produce the union from multiple registered ultrasound volumes acquired in a given cardiac-cycle phase over multiple heartbeats.

4. The medical system according to claim 1, wherein the processor is further configured to incorporate into the rendering a newly acquired volume from a known location, using the signals output by the sensor.

5. The medical system according to claim 1, wherein the processor is further configured to incorporate into the rendering a graphical indication at a known location, using the signals output by the sensor.

6. The medical system according to claim 5, wherein the graphical indication is an icon.

7. The medical system according to claim 5, wherein the graphical indication is of an artificial element.

8. The medical system according to claim 1, wherein the processor is further configured to provide multi-planar reformation (MPR) views of the portion of the organ, using the signals output by the sensor.

9. A medical imaging method, comprising:

inserting an ultrasound probe into an organ of a body, the ultrasound probe comprising:

a two-dimensional (2D) ultrasound transducer array; and a sensor configured to output signals indicative of a position and orientation of the 2D ultrasound transducer array inside the organ;

using the signals output by the sensor, registering multiple three-dimensional (3D) ultrasound volumes, acquired by the 2D ultrasound transducer array, with one another;

producing a union of the multiple registered 3D ultrasound volumes, to form a rendering of at least a portion of the organ; and presenting the rendering to a user.

10. The medical imaging method according to claim 9, wherein the rendering comprises a four-dimensional (4D) rendering of at least the portion of the organ, and wherein producing the 4D rendering comprises forming multiple instances of the union for different phases of a given heartbeat.

11. The medical imaging method according to claim 9, wherein the union is produced from multiple registered ultrasound volumes acquired in a given cardiac-cycle phase over multiple heartbeats.

12. The medical imaging method according to claim 9, and comprising incorporating into the rendering a newly acquired volume from a known location, using the signals output by the sensor.

13. The medical imaging method according to claim 9, and comprising incorporating into the rendering a graphical indication at a known location, using the signals output by the sensor.

14. The medical imaging method according to claim 13, wherein the graphical indication is an icon.

15. The medical imaging method according to claim 13, wherein the graphical indication is of an artificial element.

16. The medical imaging method according to claim 9, and comprising providing multi-planar reformation (MPR) views of the portion of the organ, using the signals output by the sensor.

* * * * *